(12) United States Patent
Yasushi et al.

(10) Patent No.: US 6,485,418 B2
(45) Date of Patent: Nov. 26, 2002

(54) HEALTH MONITORING SYSTEM

(75) Inventors: Mitsuo Yasushi, Tokyo (JP); Masatoshi Yanagidaira, Tokyo (JP)

(73) Assignee: Pioneer Corporation, Tokyo (JP)

( * ) Notice: Subject to any disclaimer, the term of this patent is extended or adjusted under 35 U.S.C. 154(b) by 74 days.

(21) Appl. No.: 09/809,352

(22) Filed: Mar. 16, 2001

(65) Prior Publication Data
US 2001/0039372 A1 Nov. 8, 2001

(30) Foreign Application Priority Data
Mar. 17, 2000 (JP) ........................................ 2000-075436

(51) Int. Cl.[7] ...................... A61B 5/0205; A61B 5/0402
(52) U.S. Cl. ...................... 600/300; 600/301; 600/515; 128/903; 128/920
(58) Field of Search ............................ 600/300, 301, 600/515; 128/903, 904, 920

(56) References Cited

U.S. PATENT DOCUMENTS

| | | | |
|---|---|---|---|
| 5,576,952 A | * 11/1996 | Stutman et al. | 600/300 |
| 5,720,771 A | 2/1998 | Snell | 607/60 |

FOREIGN PATENT DOCUMENTS

| | | |
|---|---|---|
| JP | 10-302188 | 11/1998 |
| WO | WO 99/60926 | 12/1999 |

OTHER PUBLICATIONS

European Search Report for EP 01 10 6269, dated Jul. 26, 2001.

* cited by examiner

Primary Examiner—Andrew M. Dolinar
(74) Attorney, Agent, or Firm—Morgan, Lewis & Bockius LLP

(57) ABSTRACT

A health monitoring system for communication between at least one terminal-device that moves with a person whose health is monitored and a first center device. The terminal device detects health parameters of the person, and diagnoses of the condition of health of the person in accordance with a result of the detection, and transmits the result of the diagnosis to the first center device. The first center device stores the historical diagnosis information concerning the person, receives the result of the diagnosis from the terminal device, judges whether detailed data concerning the condition of health of the person is needed in accordance with the result of the diagnosis and the historical diagnosis information, and issues a request command of the detailed data to the terminal device when it judges that the detailed data is needed.

6 Claims, 10 Drawing Sheets

HEALTH MONITORING SYSTEM

BACKGROUND OF THE INVENTION

1. Field of the Invention

The present invention relates to a health monitoring system for remotely monitoring the condition of health of a person.

2. Description of the Related Background Art

A health monitoring system for remotely monitoring the condition of health of a person whose health is to be monitored has already been well-known, and is disclosed by, for example, Japanese Laid-open Patent Publication No. 302188/1998 (Patent Kokai No. 10-302188). In the conventional health monitoring system, the condition of health of a person whose health is to be monitored is judged at regular intervals, and the judgment result is transmitted to a control center. Further, urgent and abnormal states of the person whose condition has turned for the worse are detected, and an urgent information signal is transmitted to the control center when the person is in the urgent and abnormal states.

SUMMARY OF THE INVENTION

It is therefore an object of the present invention to provide a health monitoring system which is capable of correctly judging the condition of health of each person to be monitored even when many people to be monitored exist.

The health monitoring system according to the present invention which is for communication between at least one terminal device that is moved with a person to be monitored and a first center device, wherein the terminal device includes: a sensing device for detecting health parameters of the person, a diagnosis device for diagnosing the condition of health of the person in accordance with a result of the detection of the sensing device, and a transmitter for transmitting a result of the diagnosis of the diagnosis device to the first center device; the first center device includes: a storage device for storing historical diagnosis information concerning the person, a judgment device for receiving the result of the diagnosis of the diagnosis device and for judging whether detailed data concerning the condition of health of the person is required in accordance with the received result of the diagnosis and the historical diagnosis information, and an instruction device for issuing a request command of the detailed data to the terminal device when the judgment device judges that detailed data is required.

DETAILED DESCRIPTION OF THE PREFERRED EMBODIMENT

An embodiment of the present invention will be hereinafter described in detail with reference to the attached drawings.

Figure 1:
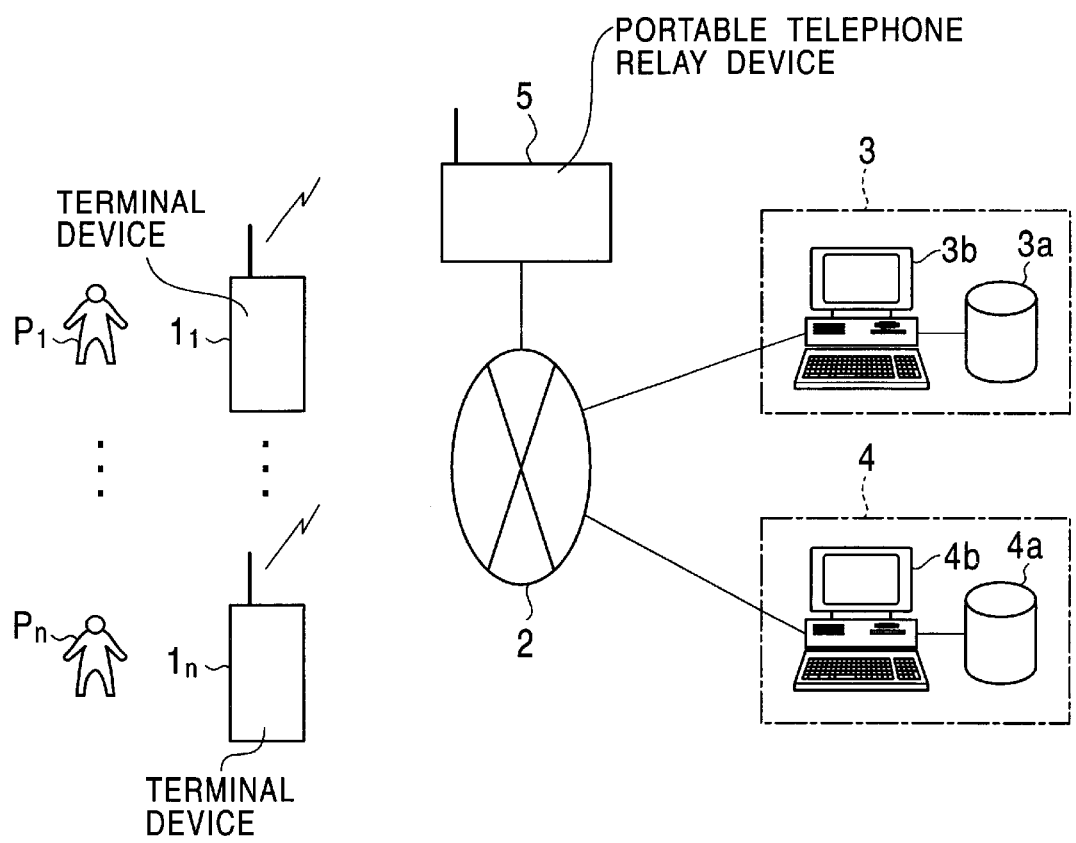
FIG. 1 is a block diagram showing a structure of the health monitoring system according to the present invention.

FIG. 1 shows a basic structure of the health monitoring system of the present invention. The health monitoring system includes portable terminal devices $1_1-1_n$, a public telephone network 2, a first center device 3, and a second center device 4. The portable terminal devices $1_1-1_n$ are carried by people $P_1-P_n$ to be monitored such as patients. The portable terminal devices $1_{11}-1_n$ are each provided with the function of a portable telephone, and are connectable to the public telephone network 2 through a relay device 5 for portable telephones. The relay device 5 is a device for establishing communication between the portable telephone and the public telephone network 2 by means of radio signals. Although a large number of relay devices including the relay device 5 are, in fact, stationed, only one relay device 5 is conveniently shown in FIG. 1. The first center device 3 and the second center device 4 are each connected to the public telephone network 2. The public telephone network 2 may be a digital network such as ISDN.

Since each of the portable terminal devices $1_1-1_n$ has the same structure, the structure of the portable terminal device 1 will be described-hereinafter.

Figure 2:
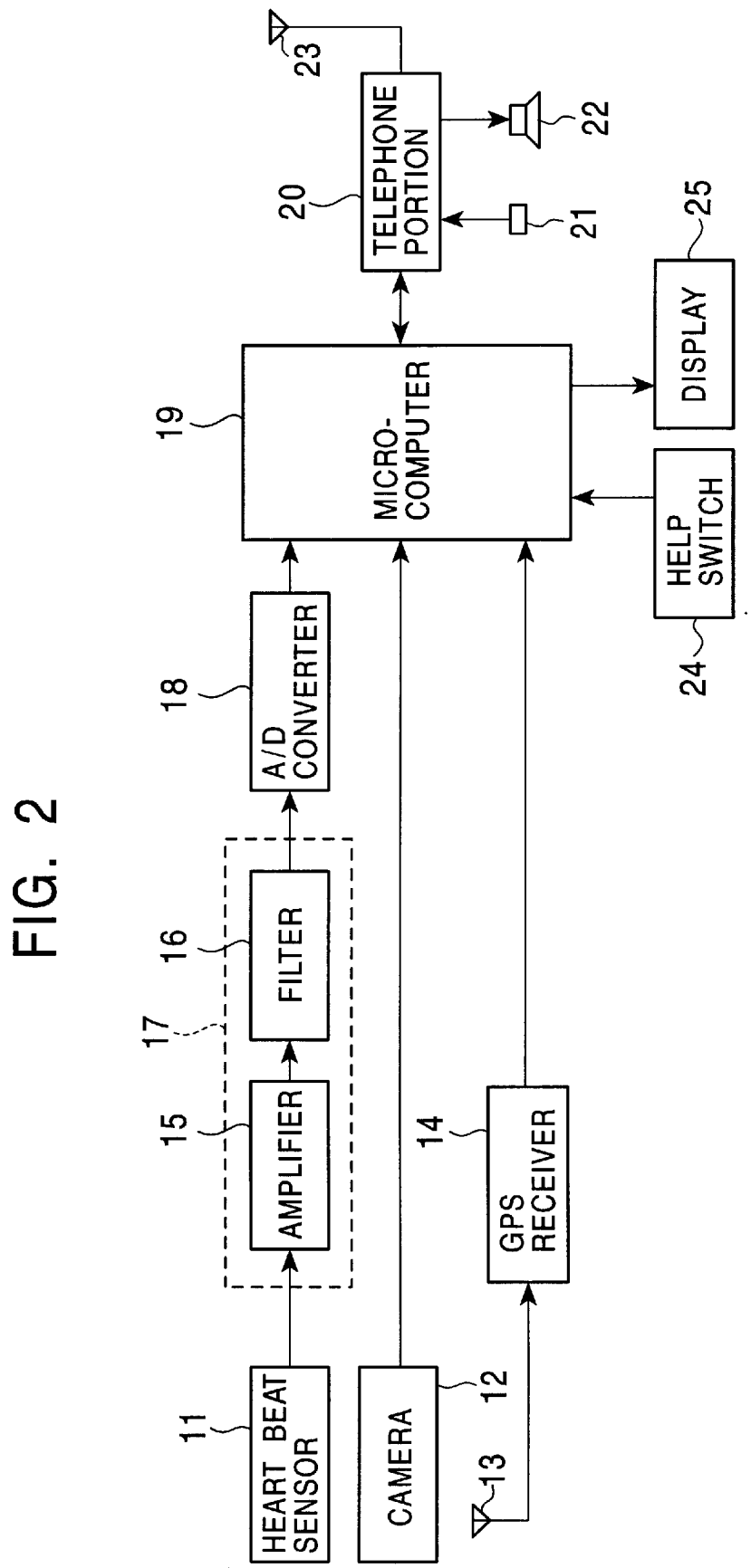
FIG. 2 is a block diagram showing a structure of a portable terminal device in the system of FIG. 1.
Figure 3:
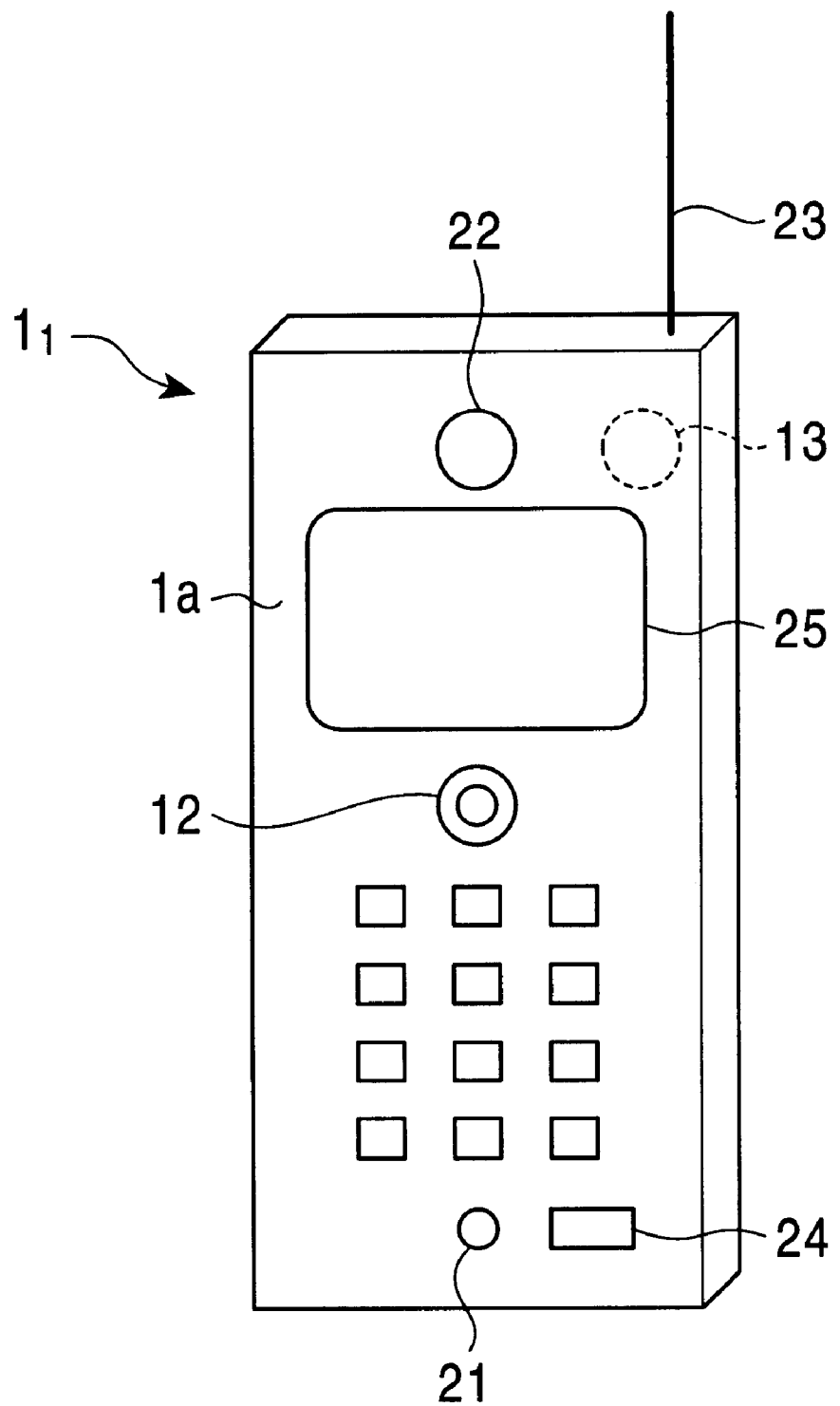
FIG. 3 shows the exterior of the portable terminal device in the system of FIG. 1.

As shown in FIG. 2, the portable terminal device 11 includes a heart beat sensor 11, a camera 12, a GPS (Global Positioning Sensor) antenna 13, and a GPS receiver 14, in order to detect the condition of health of the person $P_1$ to be monitored. The heart beat sensor 11, which is provided as a biosensor, outputs a voltage signal that indicates a potential corresponding to a heart beat of the person $P_1$. The heart beat sensor 11 is affixed to the body of the person $P_1$. The camera 12, which is a so-called digital camera, is disposed on the front of a case la of the portable terminal device $1_1$, as shown in FIG. 3, in order to detect a facial expression of the person $P_1$. The camera 12 outputs image data which is indicative of the facial expression. The GPS antenna 13 and the GPS receiver 14 are disposed to detect an action of the person $P_1$. Positional data, which indicates a current position of the portable terminal device $1_1$, i.e., a current position of the person $P_1$ to be monitored, is output from the GPS receiver 14.

A signal-processing unit 17, which includes an amplifier 15 and a filter 16, is connected to the output of the heart beat sensor 11. The signal processing unit 17 amplifies a signal output from the heart beat sensor 10, thereafter extracts only a predetermined frequency component, and outputs the component as analog heart-beat data. A microcomputer 19 is connected to the output of the signal processing unit 17 through an A/D converter 18. The signal processing unit 17 is independent of the main body of the portable terminal device $1_1$ and supplies a signal to the A/D converter 18 in the main body of the portable terminal device $1_1$ by wire or wireless.

The respective outputs of the camera 12 and the GPS receiver 14 are connected to the microcomputer 19. A help switch 24 is further connected to the microcomputer 19. The help switch 24 is a switch operated by the person $P_1$ in an emergency.

A telephone portion 20 is further connected to the microcomputer 19. The telephone portion 20 serves as a portable telephone that has a data transmission-reception function. The telephone portion 20 has an input/output terminal connected to an antenna 23 for transmission and reception, a microphone 21 for inputting a voice to be transmitted and a speaker 22 for outputting a received voice.

The first center device 3 includes a computer, and is connected to the public telephone network 2 through a modem that is not shown. The first center device 3 further includes a memory 3a that stores diagnosis data (historical diagnosis information) about each person to be monitored as a database. Likewise, the second center device 4 includes a computer and a memory 4a, and is connected to the public telephone network 2 through a modem that is not shown. If the public telephone network 2 is a digital line, a terminal adaptor is used.

An operator of the first center device 3 is a nurse, for example, and an operator of the second center device 4 is a person more medically qualified than the operator of the first center device 3. The person is a doctor, for example.

Next, the operation of the health monitoring system constructed as above will be described.

Figure 4:
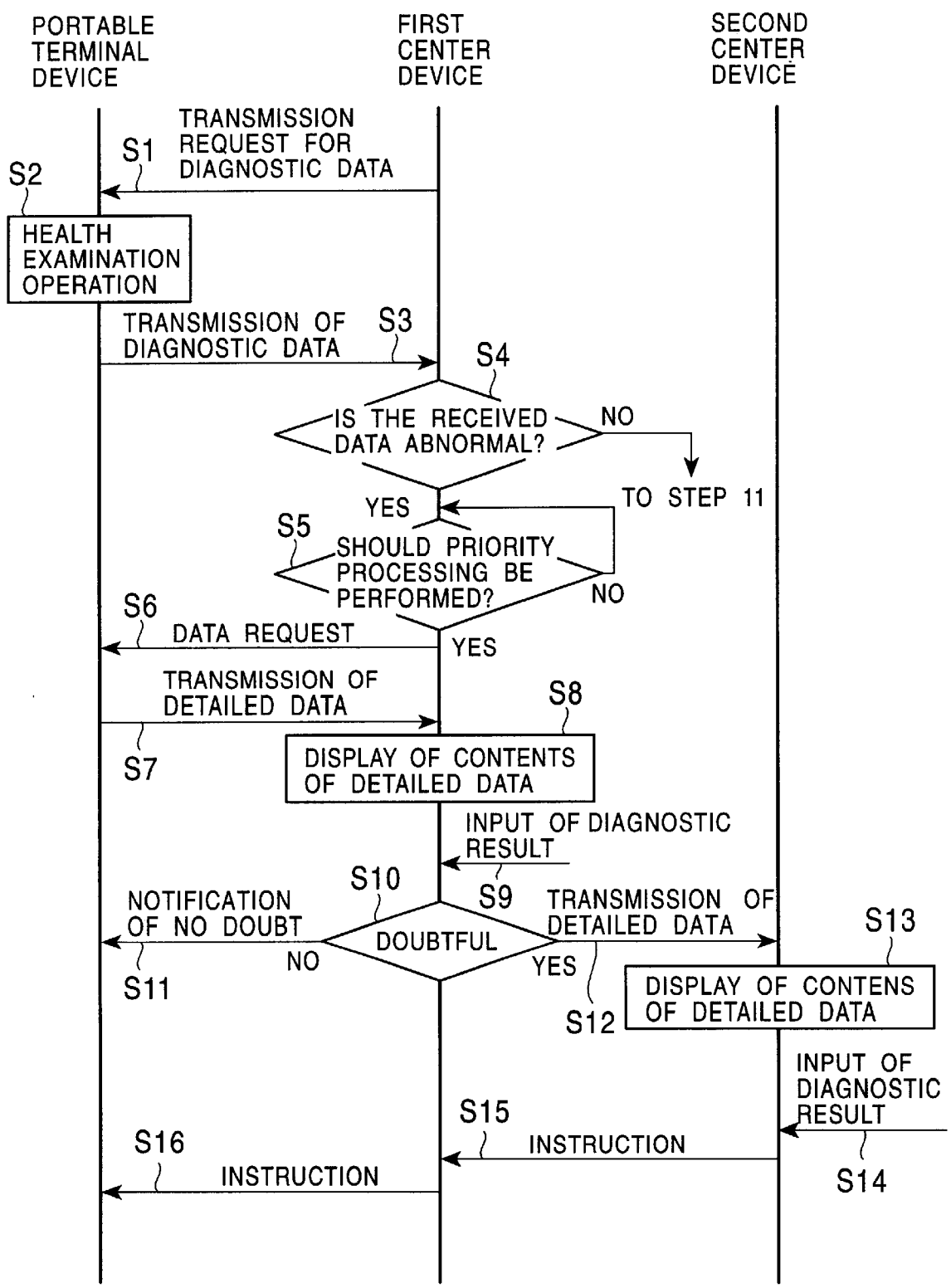
FIG. 4 is a flowchart showing the operation of the system of FIG. 1.

As shown in FIG. 4, the first center device 3 sequentially accesses each of the portable terminal devices $1_1$–$1_n$ by means of a polling operation, and requests transmission of diagnostic data. When the portable terminal device $1_1$ is requested to transmit the diagnostic data (step S1), the microcomputer 19 of the terminal device $1_1$ performs a health examination operation in response to the transmission request for the diagnostic data if (step S2).

Figure 5:
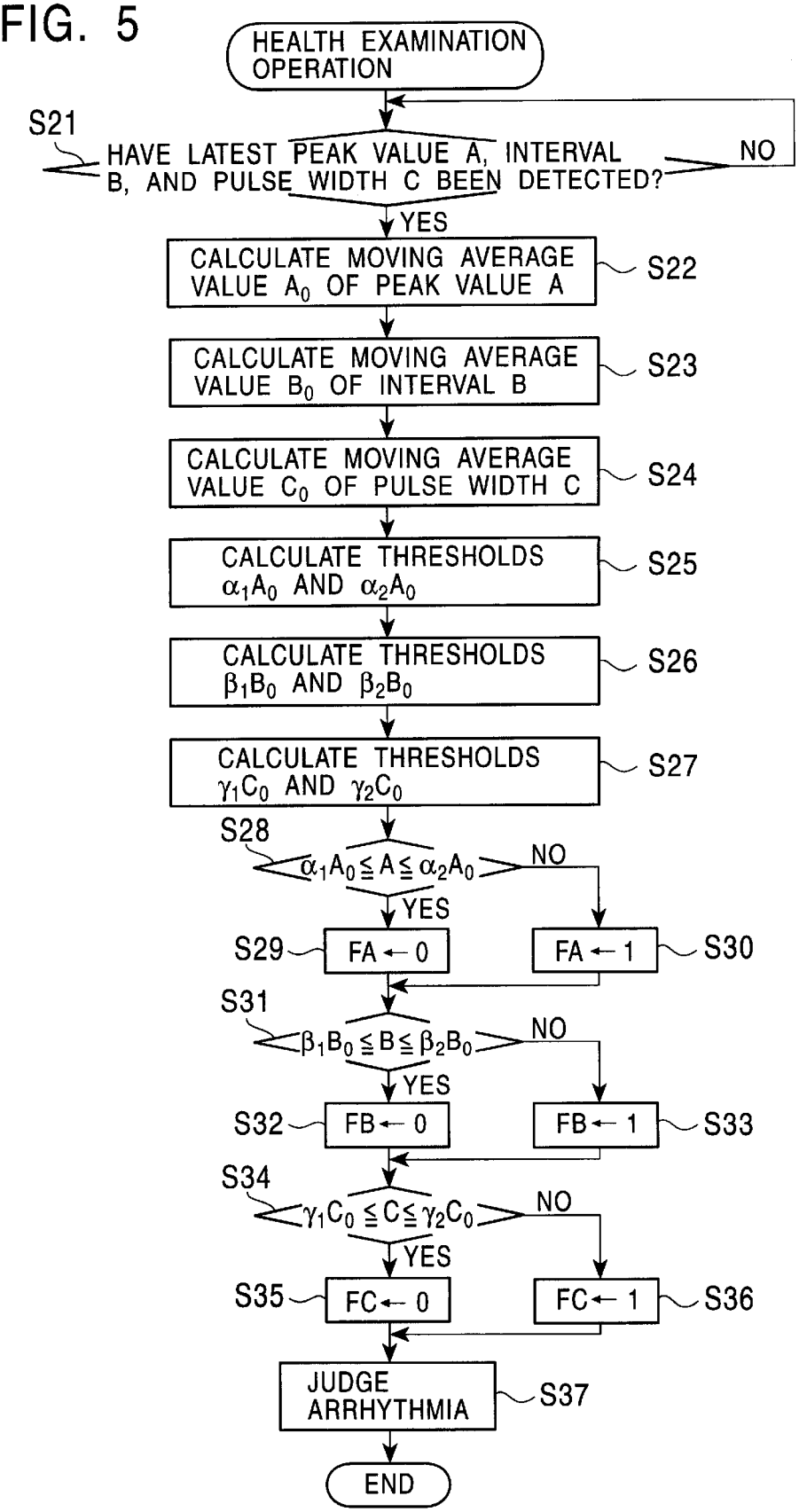
FIG. 5 is a flowchart showing the operation of a health examination.
Figure 6:
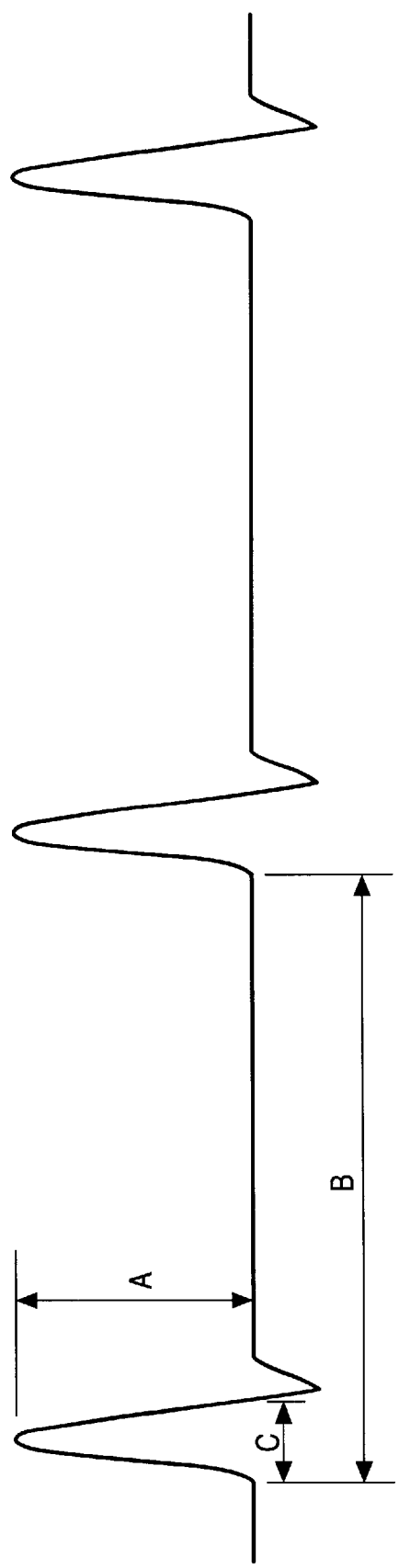
FIG. 6 shows an electrocardiogram waveform.

The microcomputer 19 of the portable terminal device $1_1$ judges whether the peak value A, interval B, and acuminate angle C of the latest pulse have been detected from heart-beat data or not, as shown in FIG. 5, in the health examination operation (step S21). The heart-beat data is supplied from the signal processing unit 17 to the microcomputer 19 through the A/D converter 18, and is sequentially stored in a memory that is not shown. Since the stored heart-beat data shows an electrocardiogram waveform as shown in FIG. 6, a pulse peak value A, interval B, and acuminate angle C are detected as the present value in the microcomputer 19 whenever a new pulse is obtained in the electrocardiogram., In practice, the acuminate angle C is detected as a pulse width C. The detected peak value A, interval B, and pulse width C are stored in the memory, with the A, B, and C grouped together as a set., by at least predetermined times including the present time (for example, 60 times) that precede the present time.

When the latest pulse peak value A, interval B, and pulse width C are detected in step S21, the moving average values $A_0$, $B_0$ and $C_0$ of the respective peak value A, interval B, and pulse width C are calculated (steps S22–S24). The moving average value $A_0$ of the peak value A is an average value of the most recent peak values A of predetermined times stored in the memory. The same average calculation is applied to the interval B and pulse width C. When the moving average values $A_0$, $B_0$, and $C_0$ are calculated, thresholds $\alpha_1 A_0$, $\alpha_2 A_0$, $\beta_1 B_0$, $\beta_2 B_0$, $\gamma_1 C_0$, and $\gamma_2 C_0$ are calculated in accordance with the moving average values $A_0$, $B_0$, and $C_0$ (steps S25–S27). $\alpha_1$, $\alpha_2$, $\beta_1$, $\beta_2$, $\gamma_1$, and $\gamma_2$ are coefficients which are previously set, where $\alpha_1 < \alpha_2$, $\beta_1 < \beta_2$, and $\gamma_1 < \gamma_2$.

It is judged whether the present peak value A is between the thresholds $\alpha_1 A_0$ and $\alpha_2 A_0$ or not (step S28). If $\alpha_1 A < A_0 \leq A \leq \alpha_2 A_0$, a flag FA is set to 0 (step S29), and if $A < \alpha_{1A0}$ or $A > \alpha_2 A_0$, the flag FA is set to 1 (step S30). It is judged whether the present interval B is between the thresholds $\beta_1 B_0$ and $\beta_2 B_0$ (step S31). If $\beta_1 B_0 \leq B \leq \beta_2 B_0$, a flag FB is set to 0 (step S32), and if $B < \beta_1 B_0$ or $B > \beta_2 B_0$, the flag FB is set to 1 (step S33). Further, it is judged whether the present pulse width C is between the thresholds $\gamma_1 C_0$ and $\gamma_2 C_0$ (step S34). If $\gamma_1 C_0 \leq C \leq \gamma_2 C_0$, a flag FC is set to 0 (step S35), and if $C < \gamma_1 C_0$ or $C > \gamma_2 C_0$, the flag FC is set to 1 (step S36).

When the flags FA to FC are obtained, the microcomputer 19 judges arrhythmia in accordance with the contents of the flags FA to FC (step S37). For example, if the flags FA to FC are all 1, pulsation is regarded as dangerous, if one or two of the flags FA to FC are 1, pulsation is regarded as needing caution, and if the flags FA to FC are all 0, pulsation is regarded as safe. The step S37 becomes a result of the health examination operation.

The microcomputer 19 in the portable terminal device $1_1$ transmits diagnostic data, which is the result of the health examination operation, to the first center device 3 (step S3). The diagnostic data is transmitted together with electrocardiogram data which consists of the heart beat data.

When the first center device 3 receives the diagnostic data from the portable terminal device $1_1$, the first center device 3 extracts diagnostic data corresponding to the person $P_1$ to be monitored from a diagnostic data group previously stored in the form of a database in the memory 3a, and, by collating the stored diagnostic data with the received diagnostic data, it is judged whether the received diagnostic data is abnormal or not (step S4). If abnormal, it is judged whether priority processing should be carried out in accordance with the level of abnormality, i.e., an urgent need (step S5). If the priority processing should be carried out, a data request is transmitted to the portable terminal device $1_1$ (step S6).

The microcomputer 19 in the portable terminal device $1_1$ responds to the data request and transmits detailed data that includes image data and positional data together with the latest electrocardiogram data to the first center device 3 (step S7). The image data indicates a facial expression of the person $P_1$ photographed by the camera 12, and the positional data indicates moving action of the person $P_1$ detected by the GPS antenna 13 and the GPS receiver 14.

Figure 7:
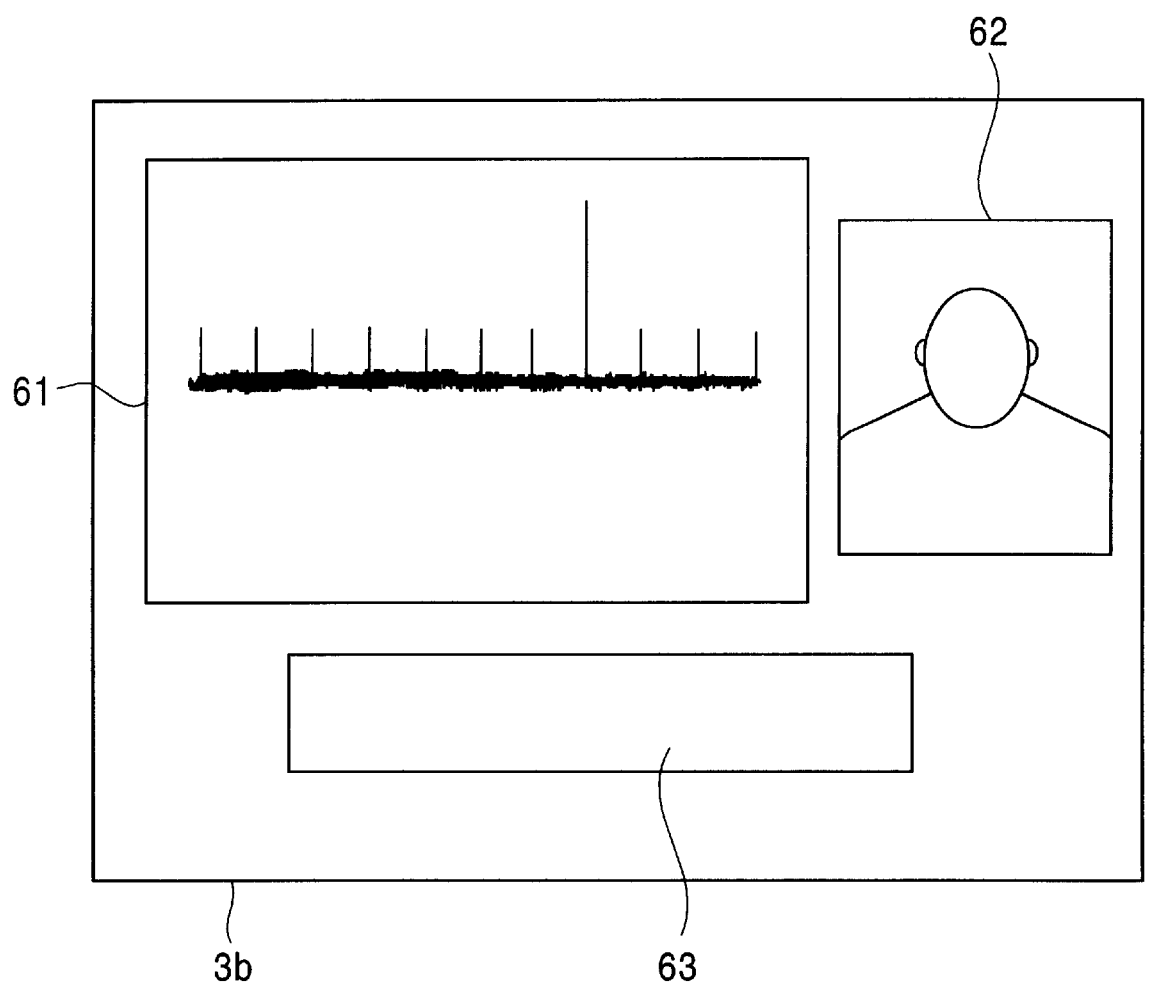
FIG. 7 shows an example in which data appear on a monitor.

When the detailed data are received, the first center device 3 displays them on the monitor 3b (step S8). Data about an electrocardiogram 61, image data 62, diagnostic data 63, etc., concerning the person $P_1$ are displayed on the monitor 3b as shown in FIG. 7. The operator diagnoses the condition of the person $P_1$ based on the displayed data. The first center device 3 accepts a result of the diagnosis given by the operator (step S9), and judges whether the result of the diagnosis is doubtful or not (step S10). If not doubtful, the portable terminal device $1_1$ is informed that the result has no doubt (step S11). The transmission of no doubt in step S11 includes a message to confirm whether there is a problem in affixing the sensor or a message to recommend a rest.

The first center device 3 received the detailed data from the portable terminal device $1_1$ only when an abnormal condition is detected by self-diagnosis in the portable terminal device $1_1$. Therefore, unnecessary data is not transmitted and received, and time required to scan the portable terminal devices $1_1$–$1_n$ by the polling operation can be shortened. Further, the detailed data are checked by the operator, such as a nurse, by the use of the past diagnostic data when an abnormal condition is detected by self-diagnosis in the portable terminal device $1_1$. Thus, proper diagnosis can be carried out.

On the other hand, if the judgment result in step S10 is doubtful, the detailed data are transmitted to the second center device 4 for further diagnosis (step S12).

When the detailed data are received, the second center device 4 displays them on the monitor 4b (step S13). The operator of the second center device 4 is an expert who is more medically qualified than the operator of the first center device 3. The operator of the second center device 4 diagnoses the condition of the person $P_1$ accordance with the data about the person $P_1$ displayed on the monitor, 4b as shown in FIG. 7, and the second center device 4 accepts a result of the diagnosis (step S14). An instruction concerning the result of the diagnosis are transmitted from the second center device 4 to the first center device 3 (step S15), and then are further supplied to the portable terminal device $1_1$ (step S16).

When the operator of the first center device 3 cannot give a proper diagnosis result to the person $P_1$ as mentioned above, the instruction by the proper diagnosis of the more qualified operator of the second center device 4 can be given to the person $P_1$.

The instruction is supplied in the form of audio data or character data. In the case of audio data, a voice is output from the speaker 22 of the portable terminal device $1_1$, and, in the case of character data, characters are displayed on a display 25.

Further, the following operations can be carried out between the portable terminal devices $1_1$–$1_n$ and the first center device 3.

Figure 8:
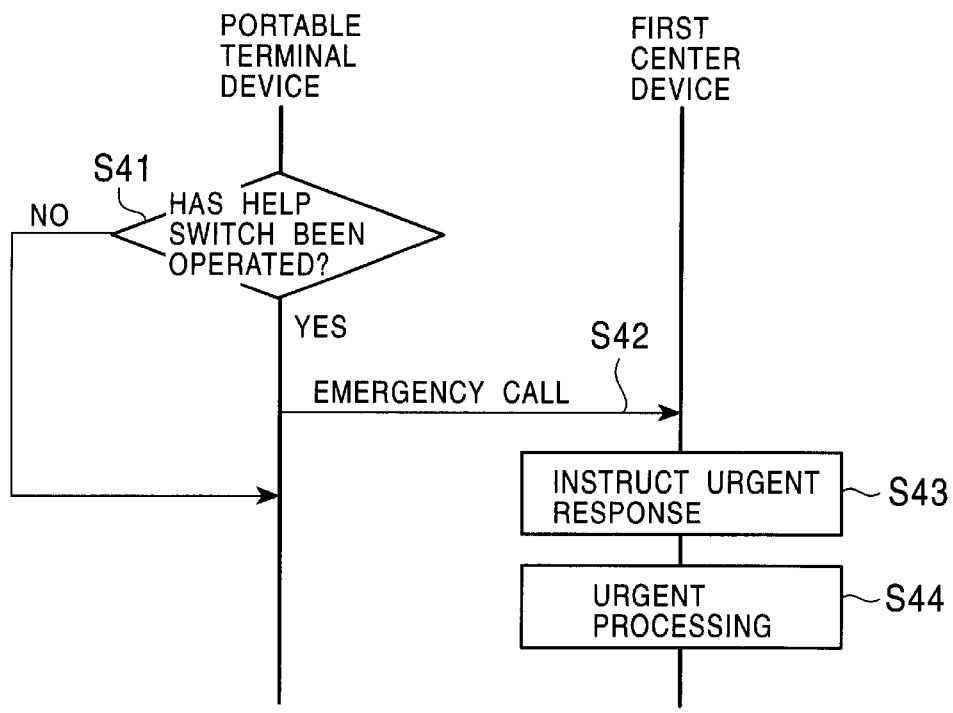
FIG. 8 is a flowchart showing the operation of the system of FIG. 1.

When the person $P_1$ to be monitored feels bodily unwell and turns on a help switch 24 of the portable terminal device $1_1$, the microcomputer 19 in the portable terminal device $1_1$ confirms the operation of the help switch 19 as shown in FIG. 8 (step S41), and an emergency call is sent to the first center device 3 (step S42). When the-emergency call is received, the first center device 3 instructs the operator to perform an urgent response (step S43). Thereafter, an urgent processing operation is carried out in accordance with manipulation of the operator (step S44). In the urgent processing, the first center device 3 has electrocardiogram data, image data, and positional data transmitted from the portable terminal device $1_1$ of the person $P_1$, and the data are transmitted to the second center device 4. As a result, an appropriate instruction is transmitted from the. operator of the second center device 4 to the person $P_1$ through the first center device 3.

Figure 9:
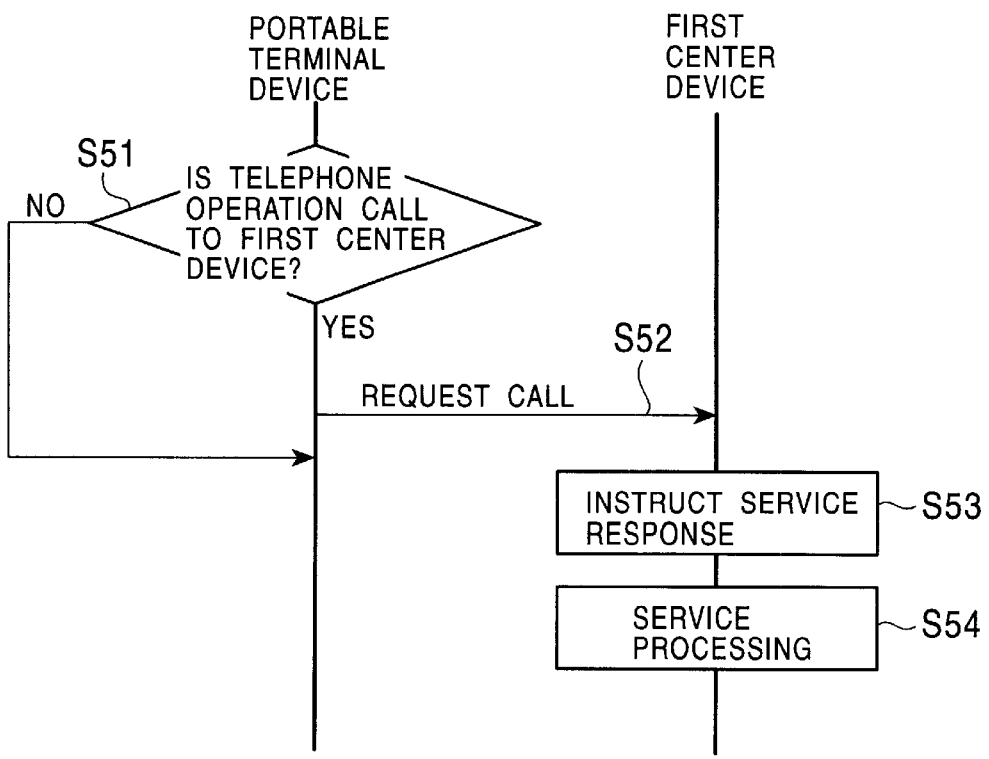
FIG. 9 is a flowchart showing the operation of the system of FIG. 1.

When the person $P_1$ calls the first center device 3 by operating a button of the portable terminal device $1_1$ in order to check his/her health, the microcomputer 19 in the portable terminal device $1_1$ confirms that it is a call to the first center device 3 (step S51), as shown in FIG. 9, and makes a request call to the first center device 3 (step S52). When the request call is received, the first center device 3 instructs the operator to perform a service response (step S53). Thereafter, a service processing operation is carried out in accordance with manipulation of the operator (step S54). In the service processing, the first center device 3 is instructed to transmit electrocardiogram data, image data, and positional data to the portable terminal device $1_1$ of the person $P_1$. The operator of the first center device 3 determines whether the person $P_1$ is in poor condition in accordance with the electrocardiogram data, image data, and positional data, or not and a result of the determination is sent back to the person $P_1$ through, for example, e-mail.

The above-mentioned embodiment has described the example in which the operator such as a nurse diagnoses the person $P_1$ while checking the data (electrocardiogram) and the detailed data (facial expression) through the first center device 2. Instead, it is possible to automatically compare data received at the current time at the first center device 2 with data stored over a long period (i.e., data corresponding to a clinical record) and judge the condition of the person $P_1$ with reference to a result of the comparison.

In addition, the above-mentioned embodiment has described the example in which a position of the person $P_1$ to be monitored is determined by the GPS antenna 13 and GPS receiver 14. Instead, it is possible to properly determine a position of the person $P_1$ by comparing the receiving levels of transmitted radio waves at a plurality of receiving stations.

In addition, the above-mentioned embodiment has described the example in which the health examination operation in step S2 is executed when polling is carried out. The health examination operation in step S2 may be always executed so that data during a certain period and judgment results are stored, and, when polling is carried out, the data during the certain period or data which has not been transmitted may be transmitted on the basis of the judgment results during the certain period.

The GPS data (positional information) obtained from the GPS receiver 14 can be transmitted not as data concerning a point but as data concerning a locus (movement line) that has been continuously recorded. Therefore, it is possible to judge abnormal condition when the locus meanders or overlaps.

Figure 10:
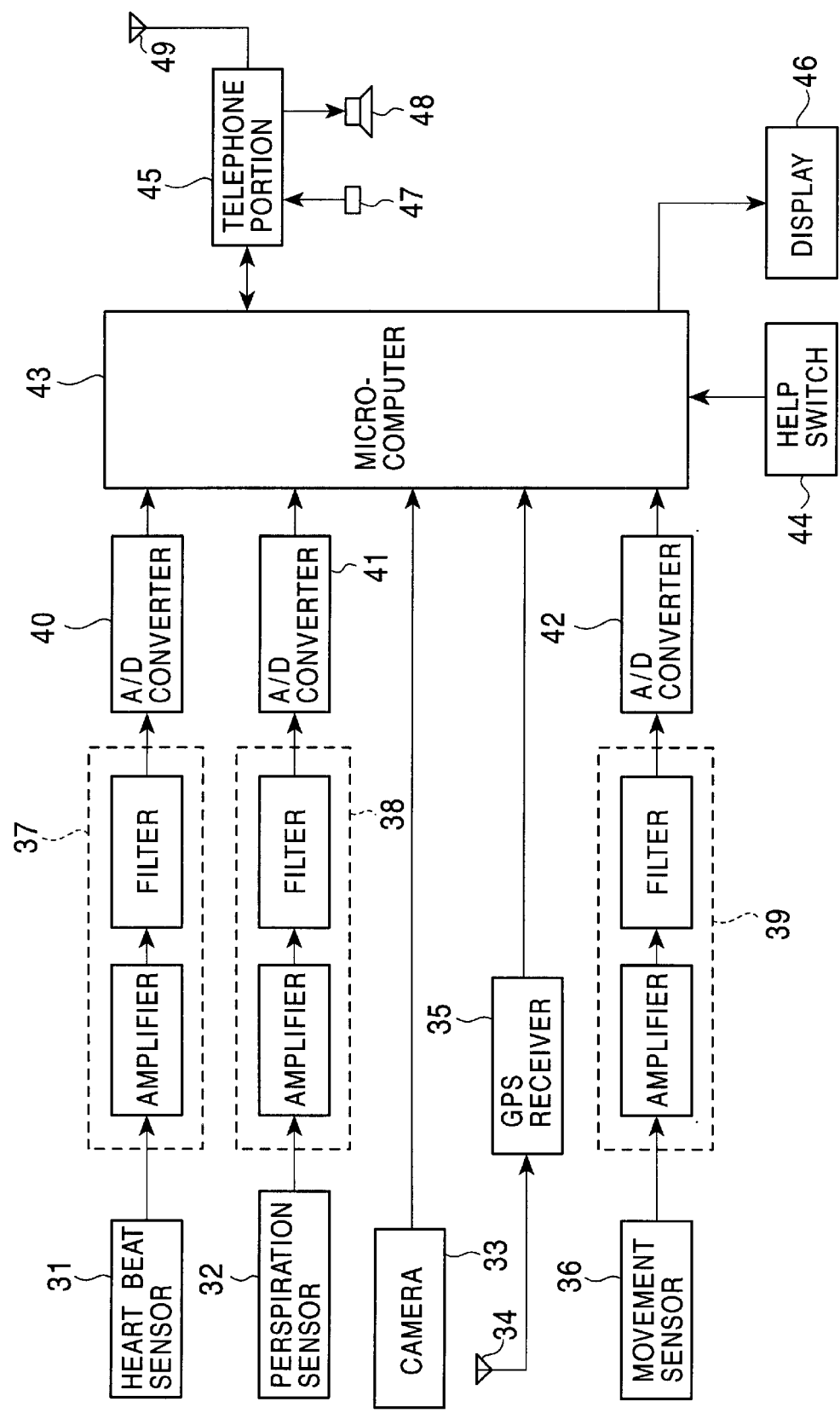
FIG. 10 is a block diagram showing a structure of an on-vehicle terminal device.

Although the person $P_1$ to be monitored is a pedestrian in the above embodiment, he/she may be a vehicle driver. If so, a terminal device of the person $P_1$ is mounted on the vehicle and is constructed as shown in FIG. 10. That is, the on-vehicle terminal device includes a heart beat sensor 31, a perspiration sensor 32, a camera 33, a GPS antenna 34, a GPS receiver 35, and a movement sensor 36 in order to detect the condition of health of the person $P_1$. The heart beat sensor 31, the perspiration sensor 32, and the movement sensor 36 are connected to a microcomputer 43 through signal processing-units 37–39, each of which includes an amplifier and a filter, and A/D converters 40–42. The camera 33 and the GPS receiver 35 are connected directly to the microcomputer 43.

Figure 11:
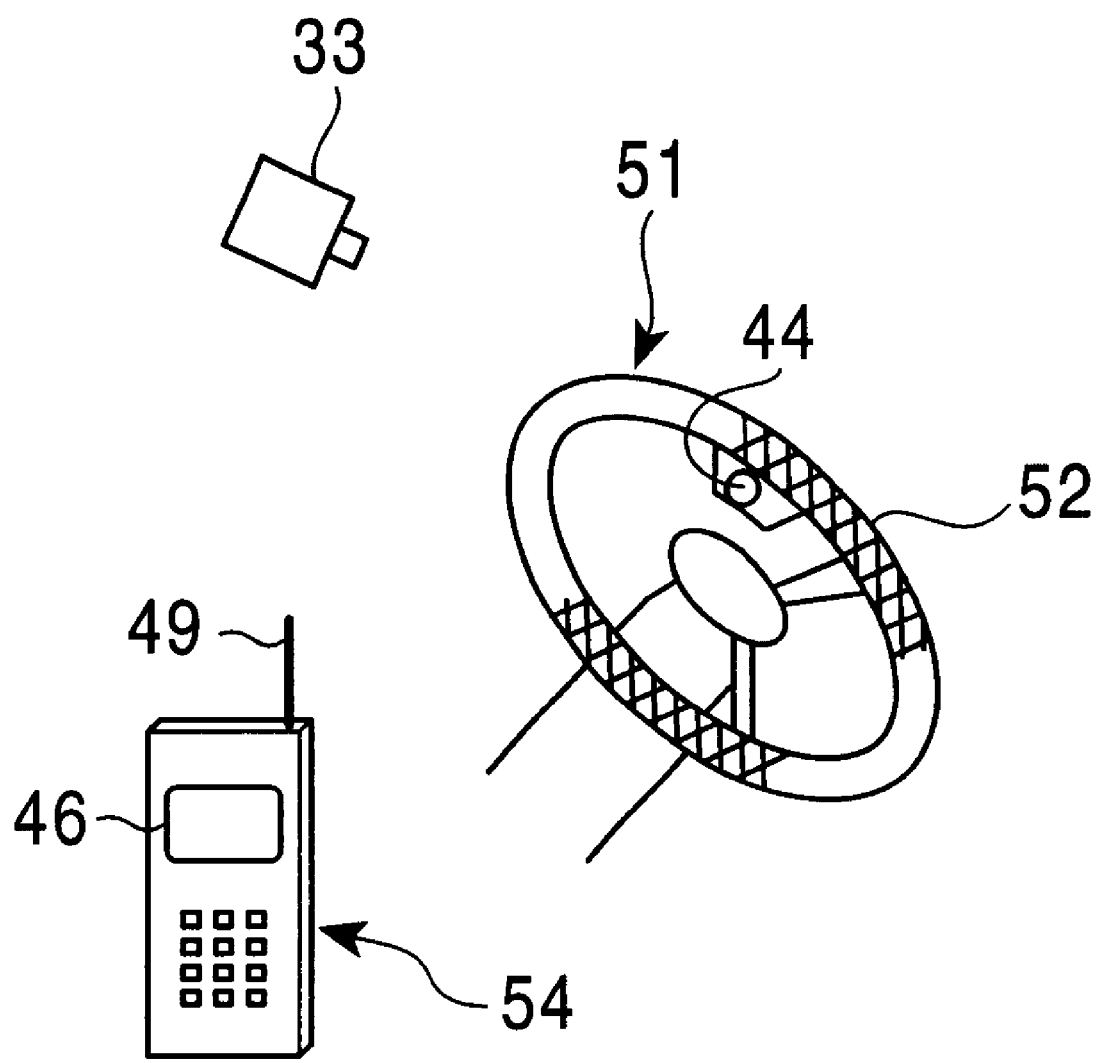
FIG. 11 shows a main body, a camera and a sensor part of the terminal device in FIG. 10.

As in the case of the heart beat sensor 11, the heart beat sensor 31 outputs a voltage signal that indicates a potential corresponding to heart beat of the person $P_1$. A detecting portion of the heart beat sensor 31 has a metallic sheet electrode 52 affixed to a grip portion of a steering wheel 51 as shown in FIG. 11, and heart-beat data is detected by allowing the palms of the person $P_1$ to be monitored to contact with the grip portion. The perspiration sensor 32 generates a voltage signal according to perspiration of the person $P_1$ by the use of the electrode 52. The camera 33 is placed on the upper portion of an interior windshield in order to detect a facial expression of the person $P_1$. The GPS antenna 34 is mounted on the outer face of the vehicle body. The movement sensor 36 serves to detect speed and acceleration of the vehicle.

As in the case of the portable terminal device $1_1$, a help switch 44, a telephone portion 45, and a display 46 are further connected to the microcomputer 43. The help switch 44 is disposed at the steering wheel 51. A microphone 47, a speaker 48, and an antenna 49 are connected to the telephone portion 45.

The signal processing units 37–39, the A/D converters 40–42, the microcomputer 43, and the telephone portion 45 are formed in a main body 54.

Since the operation of the on-vehicle terminal device constructed as above is the same as that of the above-mentioned portable terminal device $1_1$, a repetitive description thereof is omitted.

In the embodiment of the on-vehicle terminal device, measurement data can be invalidated on the basis of acceleration detected by the movement sensor 36 when the acceleration exceeds a predetermined value. Accordingly, it is possible to remove an inaccurate measurement value resulting from worsening of a measurable environment caused by, for example, vehicle vibrations.

Further, in order to prevent difficulty when driving, a guidance function by a voice synthesizer may be provided so as to aid the person $P_1$ (driver) in a measurement operation or to give instructions, such as advice based on a diagnostic result.

The heart beat sensors 11, 31 may be formed as an earring type to detect a potential according to the pulse of the person $P_1$ from the ear in the above-mentioned embodiment. Alternatively, they may be formed as a finger type to detect the potential from the finger.

In the above embodiment, arrhythmia is detected by obtaining electrocardiogram data of the person $P_1$ to be monitored. Instead, the blood pressure of the person $P_1$ may be detected to judge high blood pressure or low blood pressure and transmit the judgment data to the first center device. Alternatively, the body temperature of the person $P_1$ may be detected to judge a high body temperature or low body temperature and transmit the judgment data to the first center device.

As described above, according to the health monitoring system of the present invention, the health of a person to be monitored can be correctly judged even when a large number of people to be monitored exist.

What is claimed is:

1. A health monitoring system for communication between at least one terminal device that is moved with a person whose health is monitored and a first center device, wherein said terminal device includes: a sensing device for detecting health parameters of the person, a diagnosis device for diagnosing the condition of health of the person in accordance with a result of the detection of said sensing device, and a transmitter for transmitting a result of the diagnosis of said diagnosis device to said first center device;

said first center device includes: a storage device for storing historical diagnosis information concerning the person, a judgment device for receiving the result of the diagnosis of said diagnosis device and for judging whether detailed data concerning the condition of health of the person is required in accordance with the received result of the diagnosis and the historical diagnosis information, and an instruction device for issuing a request command of the detailed data to said terminal device when said judgment device judges that detailed data is required.

2. A health monitoring system of claim 1, wherein said terminal device transmits the result of the detection of said sensing device as the detailed data to said first center device in accordance with the request command.

3. A health monitoring system of claim 1, further comprising said second center device which is independent of said first center device, wherein said first center device includes a transmitter for transmitting the result of the diagnosis of said diagnosis device and the detailed data received from said terminal device, to said second center device in accordance with an input operation, and said second center device receives the result of the diagnosis of said diagnosis device and the detailed data supplied from said first center device and issues an instruction in accordance with the received result the diagnosis and the detailed-data.

4. A health monitoring system of claim 3, wherein said first center device transmits an instruction to said terminal device in accordance with an input operation.

5. A health monitoring system of claim 1, wherein when a plurality of terminal devices by each of which the detailed data is required exist, said judgment device judges a terminal device having a highest priority of the plurality of terminal devices in accordance with the result of the diagnosis and the historical diagnosis information, and said instruction device issues the request command to the terminal device having the higher priority.

6. A health monitoring system of claim 1, wherein said sensing device detects biological information and action pattern information as the health parameters.

* * * * *